United States Patent [19]

Oz

[11] Patent Number: 5,079,629
[45] Date of Patent: Jan. 7, 1992

[54] OPTICAL VIEWING DEVICE AND SYSTEM INCLUDING SAME

[76] Inventor: Dan Oz, 18 Vatikim Street, 40500 Even Yehuda, Israel

[21] Appl. No.: 652,765

[22] Filed: Feb. 8, 1991

[51] Int. Cl.$^5$ .............................................. H04N 7/18
[52] U.S. Cl. .................................... 358/100; 358/229
[58] Field of Search .................. 358/229, 213.13, 209, 358/98, 93, 100; 128/665, 662.06, 4, 6

[56] References Cited

U.S. PATENT DOCUMENTS

| 4,825,872 | 5/1989 | Tan | 128/665 |
| 4,830,014 | 5/1989 | Goodman | 128/665 |
| 4,837,615 | 6/1989 | Boshier | 358/100 |
| 4,898,172 | 2/1990 | Grable | 128/665 |

*Primary Examiner*—Victor R. Kostak
*Assistant Examiner*—Sherrie Hsia
*Attorney, Agent, or Firm*—Benjamin J. Barish

[57] ABSTRACT

An optical viewing system includes an optical viewing device in a housing having a socket at its inner end for application to a person's finger, a focussing lens at its outer end for focussing images in the region in front of the focussing lens, and an image sensor for transforming the images to electrical signals. A remote monitor unit receives the electrical signals and displays the images received by the image sensor.

20 Claims, 3 Drawing Sheets

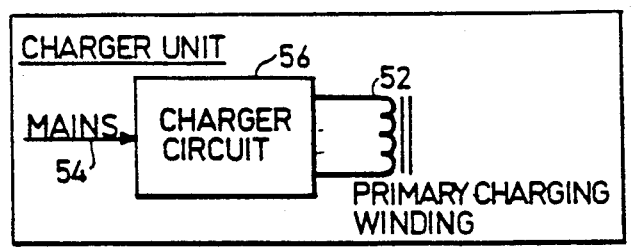
FIG 4
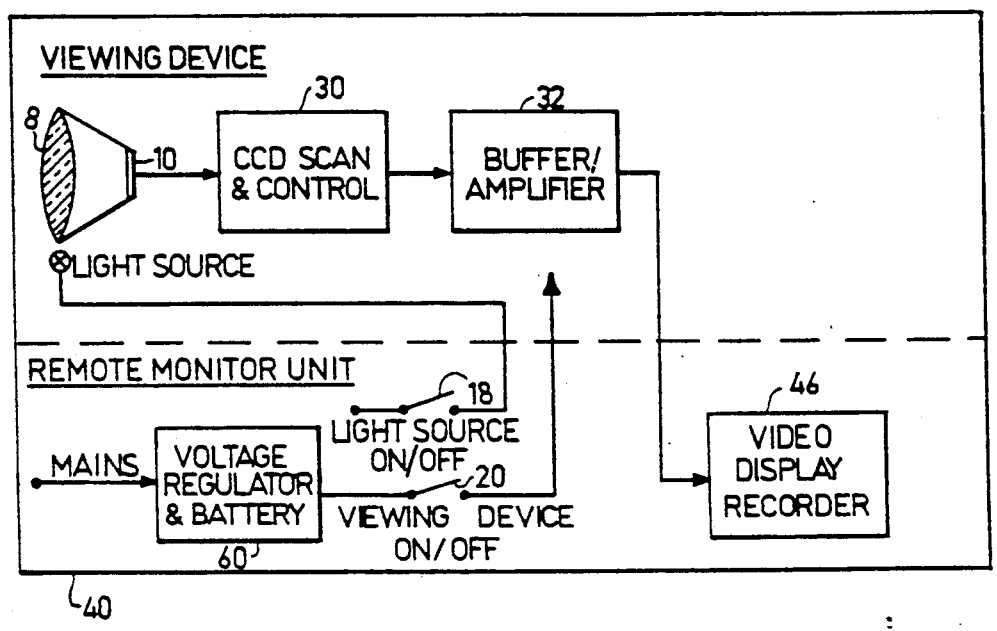
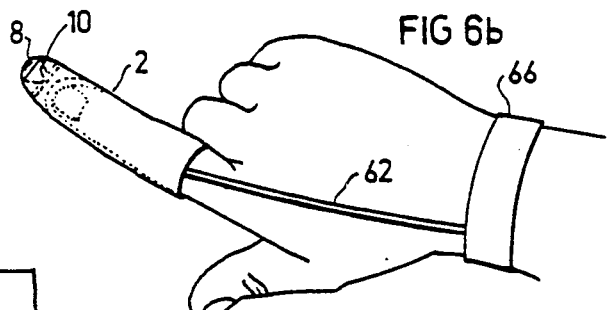
FIG 6a
FIG 6c

OPTICAL VIEWING DEVICE AND SYSTEM INCLUDING SAME

FIELD AND BACKGROUND OF THE INVENTION

The present invention relates to an optical viewing device, and also to a system including such a device.

Optical viewing devices are used in many diverse applications, such as in medical (e.g., gynecological, rectal, throat) examinations, dental examinations, automobile inspections, etc. Many such applications require viewing areas to be examined which are difficult or extremely awkward to view.

OBJECTS AND BRIEF SUMMARY OF THE PRESENT INVENTION

An object of the present invention is to provide an optical viewing device, and also a system including such a viewing device, which permit viewing particularly obscure areas in a simple and efficient manner.

According to the present invention, there is provided an optical viewing device, comprising a housing including a focussing lens and an image sensor for receiving an optical image from the focussing lens and for transforming the image to electrical signals. The housing includes a socket at one end, constituting its inner end, for application to a person's finger. The focussing lens is mounted at the opposite end of the housing, constituting its outer end, for focussing images in the region in front of the focussing lens on the image sensor.

According to further features in the preferred embodiments of the invention described below, the housing may be carried by a single socket for application to a single finger of the user. In such embodiment, it is preferable to provide the housing also with a wrist strap for securing the housing onto the user's finger. An alternative embodiment is described wherein the housing is carried by a glove of flexible material having a plurality of finger sockets for application to the user's hand.

According to further features in the preferred embodiments of the invention described below, the housing further includes a light source for illuminating the region in front of the focussing lens, and also a light switch for controlling the energization of the light source.

According to further features in the described preferred embodiments, at least the portion of the housing serving as the socket is of flexible material permitting the respective portion of the housing to conform to the shape of the user's finger. In addition, the light source includes an actuator, and the flexible portion of the housing overlies the actuator to permit energization of the light source by manually depressing the latter flexible portion of the housing. A further electric switch in the housing controls the energization of the viewing device and also includes an actuator underlying a flexible portion of the housing permitting energization of the viewing device.

According to still further features in one described preferred embodiment, the viewing device attachable to the finger of the user includes an RF transmitter and an antenna which transmits the electric signals generated by the image sensor to a remotely-located monitor unit for display. In a second described embodiment, the viewing device attachable to the user's finger is wire-connected to the remotely-located monitor unit. In both cases, the monitor unit not only displays the viewed images, but also stores such images for later inspection or further processing.

It will thus be seen that a viewing device constructed in accordance with the foregoing features extends the user's eye to the user's fingertips, thus allowing the user to see otherwise obscure places wherever the user's finger can be inserted and manipulated. For example, the user's finger can be inserted into relatively small openings or spaces and manipulated so as to direct the focussing lens to any particular area desired to be viewed. In medical applications, such a viewing device provides many advantages over conventional instruments (e.g., endoscopes), in that it can be operated only by one hand, and can be easily and precisely controlled as easy as one controls the finger (e.g., index finger) to which the device is applied.

Further features and advantages of the invention will be apparent from the description below.

BRIEF DESCRIPTION OF THE DRAWINGS

The invention is herein described, by way of example only, with reference to the accompanying drawings, wherein:

FIG. 4 is a block diagram illustrating the charging circuit for recharging the battery in the viewing device of FIG. 1;

FIG. 5 is a block diagram illustrating a viewing system in which the monitor unit is wire-connected to the viewing device; and FIGS. 6a, 6b and 6c illustrate examples of three arrangements for mounting the viewing device on the user's finger.

DESCRIPTION OF PREFERRED EMBODIMENTS

Figure 1:
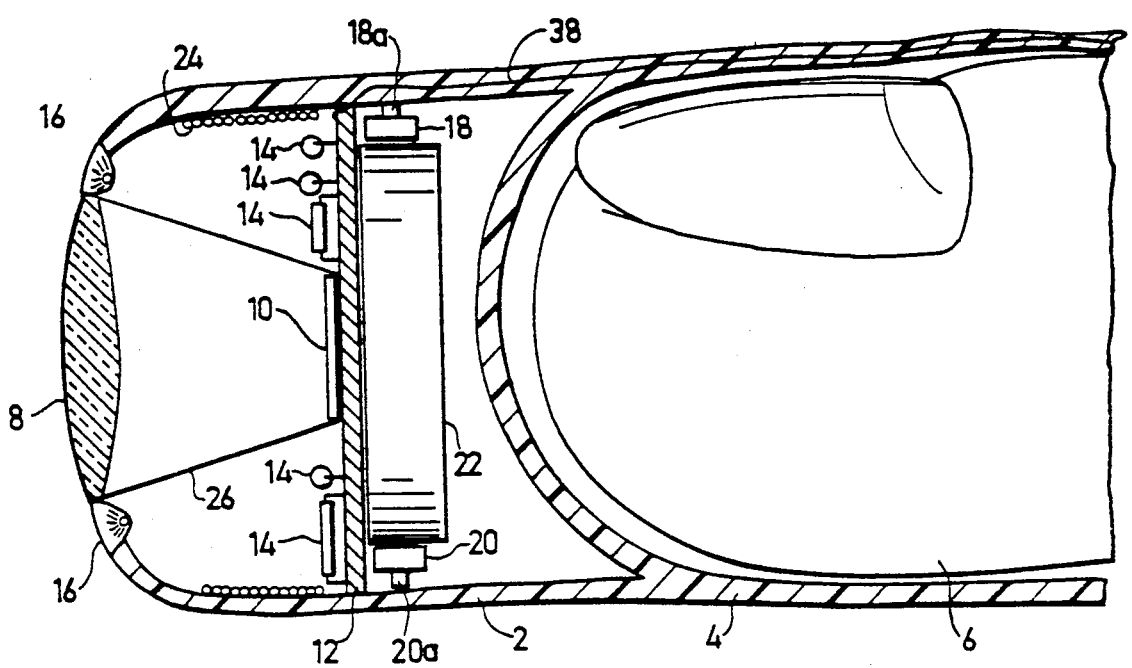
FIG. 1 is a longitudinal sectional view illustrating one form of viewing device constructed in accordance with the present invention.

The optical viewing device illustrated in FIG. 1 of the drawings comprises a housing, generally designated 2, formed at its rear end with a socket 4 for application to a person's finger 6. The front end of housing 2 carries a focussing lens 8 for focussing optical images in front of the lens onto a planar image sensor 10 mounted to a printed circuit board 12 secured within the housing between the focussing lens and socket. Printed circuit board 12 also carries the electronic components of the device, schematically indicated at 14 in FIG. 1.

The front end of housing 2 further carries an annular light source 16 around of the focussing lens 8. Light source 16 is adapted to illuminate the space in front of the focussing lens 8 to be imaged by the lens onto the image sensor 10.

Printed circuit board 12 further carries an electric switch 18 including an actuator 18a which is actuated in order to energize the light source 16, and a further electric switch 20 including an actuator 20a which is actuated in order to energize the viewing device. The electric circuitry is powered by a rechargeable battery 22 also carried by the printed circuit board 12 and rechargeable by a winding 24 secured within the front part of housing 2 between the focussing lens 8 and the printed circuit board 12.

Housing 2 is made of a flexible elastomeric material, such as rubber, enabling its socket 4 to firmly grip the user's finger 6. The flexibility of housing 2 also enables the switches 18 and 20 to be selectively actuated by merely pressing the portion of housing 2 overlying their actuators 18a, 20a.

Image sensor 10 is a CCD (charge coupled device), as commonly used in solid-state televison cameras. CCD 10 receives the optic image focussed onto it by focussing lens 8 and transforms the image into electrical signals. An opaque light shield 26 extending between the focussing lens 8 and the CCD 10 prevents stray light from being received on the CCD.

Figure 2:
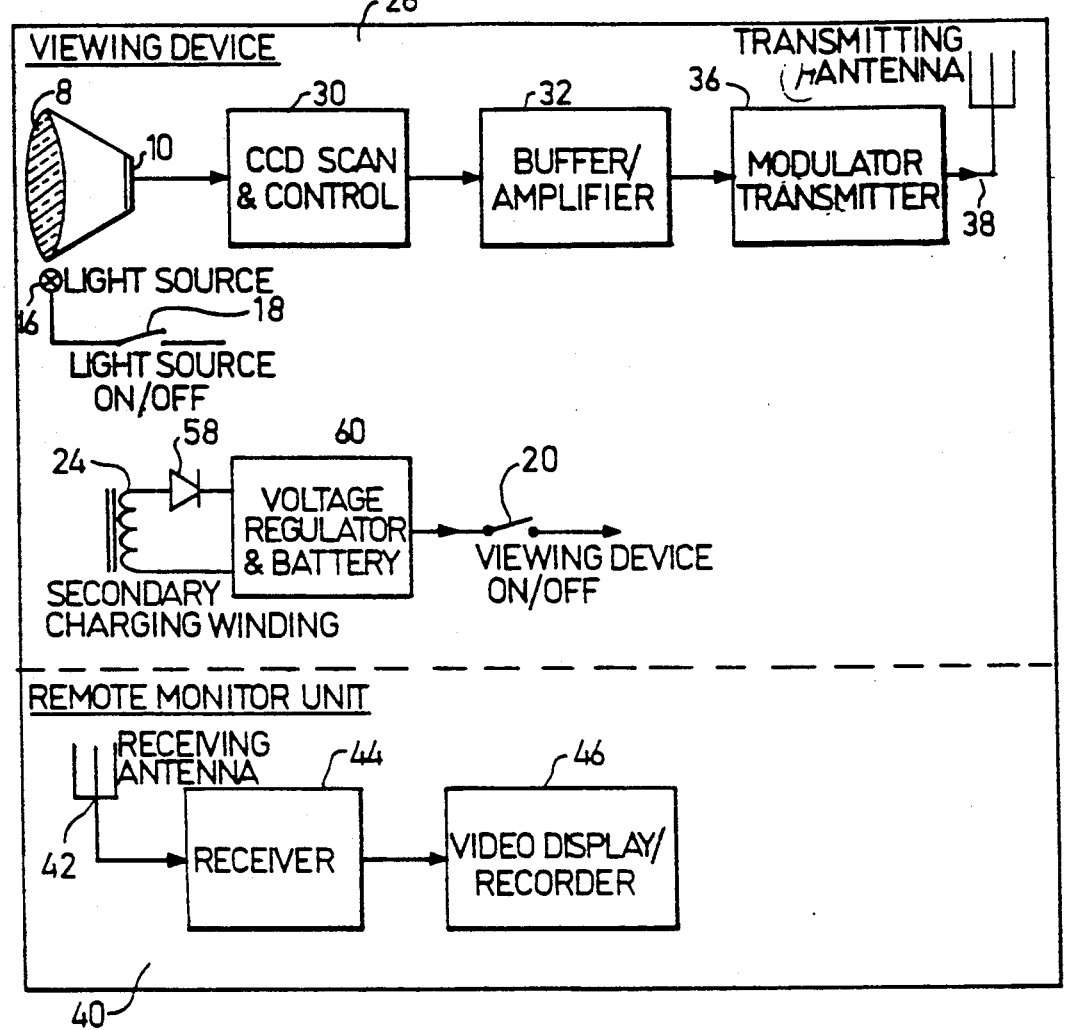
FIG. 2 is a block diagram illustrating the circuit in the viewing device of FIG. 1, and in the monitor unit to be used with the viewing device.

FIG. 2 more particularly illustrates the electrical circuitry carried by the printed circuit board 12 within housing 2. This electrical circitry includes a CCD scan and control unit 30, a buffer/amplifier unit 32, and a modulator/transmitter unit 36. Unit 36 modulates the electrical signals from the CCD 10 onto an RF carrier wave, and transmits the signal through space via a transmitting antenna 38. As shown in FIG. 1, transmitting antenna 38 may be an electrical conductor embedded within the rubber housing 2.

A remote monitor unit, generally designated 40 in FIG. 2, is located at any convenient location remote from housing 2. The monitor unit includes a receiving antenna 42, a receiver unit 44 which detects the signal and transfers it to a video display/recorder unit 46. Unit 46 displays the image sensed by the CCD image sensor 10, and, if desired, also records the video signals for later examination and/or processing.

The manner of using the viewing system illustrated in FIGS. 1 and 2 will be apparent from the above description. Thus, housing 2 may be applied by inserting the user's fingers (e.g., index finger) into socket 4. The housing 2 may then be inserted into the space to be viewed and manipulated as desired by moving the finger so as to view any space of interest in front of the focussing lens 8. If the ambient light is insufficient, the artificial light source 16 carried by housing 2 may be energized by depressing the portion of housing 2 overlying switch actuator 18a to actuate the light switch 18. The electrical circuitry within housing 2 may be energized in a similar manner, by depressing the portion of housing 2 overlying actuator 20a to actuate its switch 20.

It will thus be seen that the device illustrated in FIG. 1 may be used for viewing any normally hard-to-reach spaces, so that the particular area to be viewed is aligned with focussing lens 8 which focusses the image onto the CCD image sensor 10. The latter sensor is controlled by the scan and control unit 30 of FIG. 2, and outputs electrical signals which are amplified in amplifier 32, modulated in an RF carrier wave in unit 36, and transmitted through space via the transmitting antenna 38. The so-transmitted signals are received by antenna 42 of the remote monitor unit, detected in its receiver 44, and then displayed or recorded in the video display/recorder unit 46.

Figure 3:
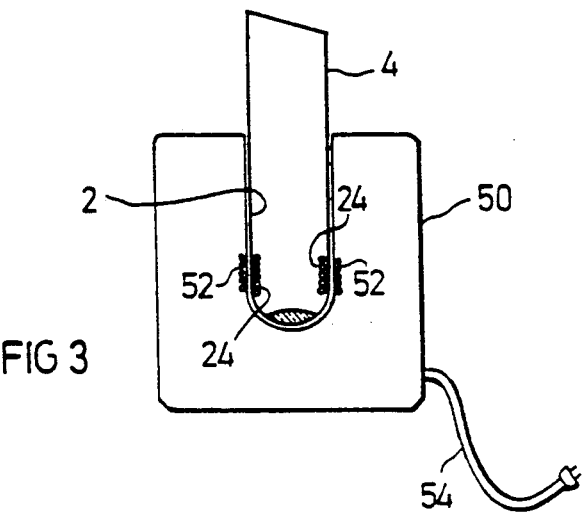
FIG. 3 illustrates how the viewing device of FIG. 2 may be recharged between uses.

Whenever the illustrated system is not in use, its battery 22 may be recharged by merely inserting the front end of housing 2 into a housing 50 (FIG. 3) containing the primary winding 52 of a transformer charger in alignment with the secondary charging winding 24 within housing 2. Charger unit 50 includes electric conductor 54 connectible to the supply mains, and a charger circuit 56 connecting the primary winding 52 of the charging transformer to the supply mains. The secondary winding 24, located within housing 2 of the viewing device, is connected via a rectifier 58 to the voltage regulator unit 60 which includes the battery (22, FIG. 1) for recharging the battery. The latter circuit is controlled by the ON/OFF switch 20.

FIG. 5 illustrates a second embodiment of the invention, very similar to that of FIGS. 1-4, and therefore generally identified by the same reference numerals in order to facilitate understanding. The main difference in the embodiment of FIG. 5, over that of FIGS. 1-4, is that the viewing device 28, carrying the socket 4 for attachment to the user's finger, is wire-connected to the remote monitor unit 40. Accordingly, the viewing device 28 does not include a rechargeable battery but rather is powered by the main supply line via the wire connection from the monitor unit 40 to the viewing unit. The embodiment of FIG. 5 therefore does not need a battery recharging circuit. In substantially all other respects, the construction and operation of the system of FIG. 5 are the same as described above with respect to FIGS. 1-4.

FIG. 6a illustrates the optical receiving device described above, including the housing 2 and its socket 4 for application to the finger of the user, with the focussing lens 8 at the front tip of the unit so that it can be manipulated to view any space that might otherwise be difficult or even impossible to view by conventional means. As indicated earlier, the housing 2 could also include an antenna if the signals are to be transmitted through space.

FIG. 6b illustrates the same arrangement as in FIG. 6a, with the housing 2 applied to the index finger of the user. In this case, however, the unit further includes a strap 66 applied to the user's wrist and connected to the finger-applied housing 2 by a connecting strip 62 to prevent accidental detachment of housing 2 from the user's finger. The connecting strip 62 may also include the antenna conductors 38 if that unit is to be of the RF type described above with respect to FIGS. 1-4, to include the RF transmitter for transmitting the image signals to a remotely-located monitor unit via a space link.

FIG. 6c illustrates an arrangement wherein housing 2 is carried by a glove 64 of flexible material, e.g., rubber, having a plurality of finger sockets, one of which carries the optical receiving unit (and antenna, if included), for application to the user's hand.

While the invention has been described with respect to several preferred embodiments, it will be appreciated that these are set forth merely for purposes of example, and that many other variations, modifications and applications of the invention may be made.

What is claimed is:

1. An optical viewing device, comprising: a housing including a focussing lens and an image sensor for receiving optical images from said focussing lens and for transforming the images to electrical signals; characterized in that said housing includes a socket at one end, constituting the inner end of the housing, for application to a person's finger; and said focussing lens is mounted at the opposite end of the housing, constituting its outer end, for focussing optical images in the region in front of the focussing lens on the image sensor.

2. The device according to claim 1, wherein said housing further includes a light source for illuminating the region in front of the focussing lens.

3. The device according to claim 2, wherein said housing further includes a light switch for controlling the energization of said light source.

4. The device according to claim 3, wherein at least the end of the housing including said socket is of flexible material permitting it to conform to the shape of the user's finger.

5. The device according to claim 4, wherein said light switch includes an actuator, and said housing includes a flexible portion which overlies said actuator so as to permit energization of the light source by manually depressing said latter flexible portion of the housing.

6. The device according to claim 5, wherein said housing includes a further electric switch controlling the energization of said viewing device, said further electric switch also including an actuator underlying said flexible portion of the housing permitting energization of the viewing device by manually depressing said latter flexible portion of the housing.

7. The device according to claim 1, wherein said housing is carried by a single socket for application to a single finger of the user.

8. The device according to claim 7, wherein said housing further includes a wrist strap for securing the housing onto the user's finger.

9. The device according to claim 1, wherein said housing is made of flexible material.

10. The device according to claim 1, wherein said housing is carried by a glove of flexible material having a plurality of finger sockets for application to the user's hand.

11. The device according to claim 1, wherein said housing further includes a battery for energizing said image sensor.

12. The device according to claim 11, wherein said battery is of the rechargeable type, and said housing includes a charging circuit comprising a charging secondary winding adapted to be placed in close proximity to a charging primary winding of an external charging circuit in order to recharge said battery.

13. The device according to claim 11, wherein said housing further includes an RF transmitter and antenna for transmitting the electric signals from said image sensor.

14. The device according to claim 13, in combination with a monitor including an RF receiver and antenna for receiving said electric signals transmitted by the optical viewing device.

15. The device according to claim 1, in combination with a monitor wire-connected to the output of said image sensor.

16. The device according to claim 1, wherein said image sensor is a CCD.

17. An optical viewing system comprising:
an optical viewing device; and a remotely-located monitor device;
said optical viewing device comprising a housing including:
a socket at one end, constituting the inner end of the housing, for application to a person's finger;
a focussing lens at the opposite end of the housing, constituting its outer end, for focussing optical images in the region in front of the focussing lens;
and an image sensor within the housing for receiving optical images from said focussing lens and for transforming the images to electrical signals;
said monitor unit including an optical display for displaying the images received by said image sensor.

18. The system according to claim 17, wherein said optical viewing device further includes a light source for illuminating the region in front of the focussing lens, and a light switch for energizing said light source.

19. The system according to claim 17, wherein said optical viewing device further includes an RF transmitter for transmitting the electric signals from the image sensor; and said monitor unit includes an RF receiver for receiving said transmitted RF signals and for feeding them to the display.

20. The system according to claim 17, wherein said monitor unit is wire-connected to said optical viewing device.

* * * * *